(12) United States Patent
Barresi et al.

(10) Patent No.: US 8,117,005 B2
(45) Date of Patent: Feb. 14, 2012

(54) OPTIMIZATION AND CONTROL OF THE FREEZE-DRYING PROCESS OF PHARMACEUTICAL PRODUCTS

(75) Inventors: Antonello Barresi, Collegno (IT); Giancarlo Baldi, Turin (IT); Marco Parvis, Biella (IT); Alberto Vallan, Pralungo (IT); Salvatore Velardi, Rivarolo Canavese (IT); Hassan Hammouri, Coublevie (IT)

(73) Assignees: Politecnico Di Torino, Torino (IT); Universite Claude Bernard Lyon 1, Villeurbanne Cedex (FR)

( * ) Notice: Subject to any disclaimer, the term of this patent is extended or adjusted under 35 U.S.C. 154(b) by 580 days.

(21) Appl. No.: 12/296,802

(22) PCT Filed: Apr. 10, 2007

(86) PCT No.: PCT/IB2007/051276
§ 371 (c)(1),
(2), (4) Date: Oct. 10, 2008

(87) PCT Pub. No.: WO2007/116371
PCT Pub. Date: Oct. 18, 2007

(65) Prior Publication Data
US 2009/0276179 A1 Nov. 5, 2009

(30) Foreign Application Priority Data

Apr. 11, 2006 (IT) .............................. TO20006A0270

(51) Int. Cl.
*G01K 17/00* (2006.01)
*G01K 3/00* (2006.01)

(52) U.S. Cl. ....................................... 702/136; 374/137

(58) Field of Classification Search .................. 702/136, 702/81, 84, 127, 130–131, 133, 179, 182–183, 702/188–189; 34/60, 92, 282, 284, 286–287, 34/292, 493–495, 497; 62/100, 268; 340/501–502, 340/531, 539.1, 539.26–539.27, 870.01–870.02, 340/870.05, 870.17; 374/1–2, 10, 20, 29–30, 374/32, 100–101, 107, 110–112, 124, 132, 374/137, 163, 165–166, 179, 186, 189, 208; 703/2, 4, 11
See application file for complete search history.

(56) References Cited

U.S. PATENT DOCUMENTS
4,475,024 A 10/1984 Tateda
(Continued)

OTHER PUBLICATIONS

Velardi et al., A Non-Linear Observer for Real-Time Monitoring and Control of the Freeze-Drying Process of Pharmaceuticals in Vial, May 12-13, 2005, Proceedings of AFSIA/EFCE Drying Conference, 3 pp.*

(Continued)

*Primary Examiner* — Mohamed Charioui
*Assistant Examiner* — Toan Le
(74) *Attorney, Agent, or Firm* — Sughrue Mion, PLLC

(57) ABSTRACT

A system for monitoring the lyophilization process of a product in containers (4, 4a, 4b) arranged inside a lyophilization chamber, including a temperature measurement system (6) associated with each container housed inside (10) the lyophilization chamber, capable of surveying local temperature data for each container. The system includes a wireless communication system (8) for the surveyed temperature data and a processing module (16) for said data, located externally to the lyophilization chamber, programmed to determine at least one parameter indicative of the progress of the lyophilization process not measured by the measurement system, through the use of a predetermined representation model of the process, capable of correlating a local temperature value of the container with the parameter.

12 Claims, 4 Drawing Sheets

U.S. PATENT DOCUMENTS 7,520,670 B2 * 4/2009 Schwegman .................. 374/150

OTHER PUBLICATIONS

Carullo, et al., "An analytical balance for lyophilisation systems," Instrumentation and Measurement Technology Conference, held in St. Paul, Minnesota, May 18-21, 1998, Conference Proceedings, p. 243-248, vol. 1, XP010281596.

Orville C. Sandall et al., "The Relationship Between Transport Properties and Rates of Freeze-Drying of Poultry Meat", AiChE Journal, May 1967, p. 428-438, vol. 13, No. 3.

James E. Hill et al., "Sublimation-Dehydration in the Continuum, Transition and Free-Molecule Flow Regimes", Int. J. Heat Mass Transfer, 1971, pp. 625-638, vol. 14.

* cited by examiner

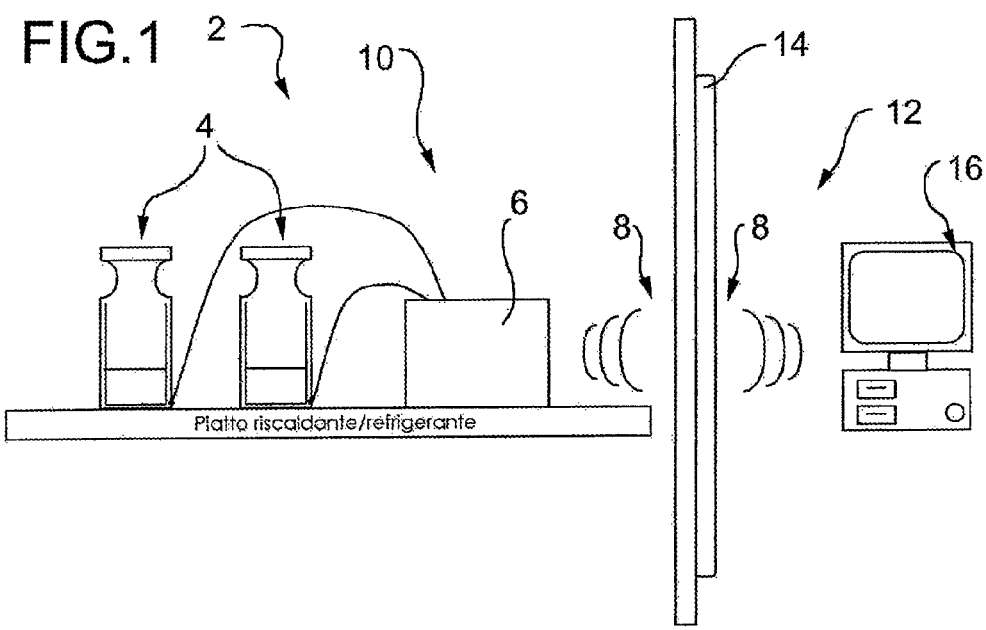
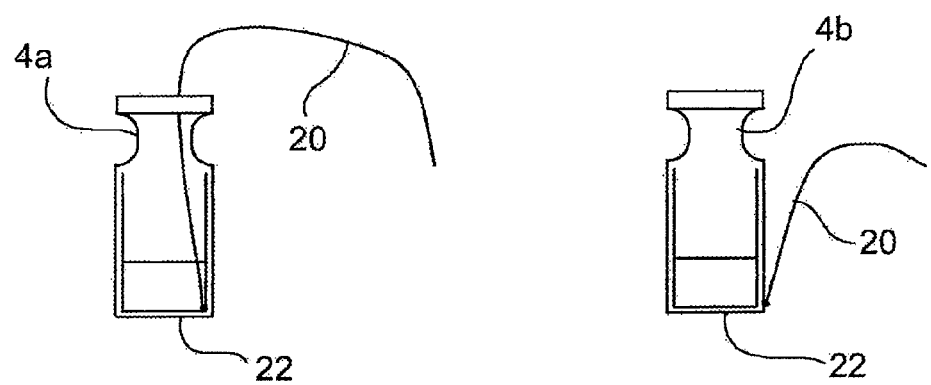

OPTIMIZATION AND CONTROL OF THE FREEZE-DRYING PROCESS OF PHARMACEUTICAL PRODUCTS

BACKGROUND OF THE INVENTION

The present invention relates to a system for monitoring the lyophilisation process of pharmaceutical products contained in vials and ampoules.

Lyophilisation is a well known drying process wherein the solvent, generally water, is removed by means of sublimation from the previously frozen product, by exploiting the combined action of low temperature and low pressure. It is useful to monitor the lyophilisation process in that this allows controlling the quality of the product and allows the development and implementation of specific optimisation and control strategies for the process itself. The temperature of the product is the most important variable to be monitored during the process. Indeed, the sublimation phase, known as primary drying, must be carried out at such a temperature as to avoid the formation of liquid, so that the fraction of the product already dried does not deteriorate thermally and break down.

Another important process variable is the position of the sublimation front within the product subjected to lyophilisation, which moves during the process, travelling from the top of the container to the bottom, until it disappears as soon as the frozen solvent has been completely removed. Hence, monitoring the position of the sublimation interface allows determining the state of progression of the primary drying phase and allows the establishment of when the sublimation process has terminated.

Two methods are used nowadays, at both the industrial and laboratory levels, for measuring the temperature of a product in a container associated with an external heating element (plate).

A first method consists of inserting a thermocouple inside the container. A thermocouple is inserted inside the container containing the product in the liquid state, generally placed in contact with the inner surface at the base of the container, or in another position. The value of the temperature measured is assumed to be representative of that of the entire product, even if a temperature gradient exists between the base of the container and the sublimation front, which is not known a priori. This measurement method is invasive, whereby the thermocouple disturbs both the exchanges of heat which are established between the various parts of the system and the physical freezing process. Indeed, even though the insertion of thin thermocouples into the vial is a widely used method for measuring the temperature of the product, it is well known that this procedure produces a change in the elementary nucleation phenomena and in the growth of ice crystals. The tip of the thermocouple acts as a heterogeneous nucleation site, and this leads to an increase in the mean ice crystal size, which leads to reduced matter transfer resistance during the primary drying phase. Furthermore, the presence of the probe body causes the formation of a preferential path for the water vapour molecules, causing a further reduction of mass transfer resistance in the dry layer. All the above effects lead to faster drying kinetics in relation to the monitored vials which, as a consequence, cannot be considered to be representative of the entire process. Furthermore, the insertion of the probe can compromise the sterility of pharmaceutical products.

A second method used involves measuring the temperature manometrically, and is known as "Manometric Temperature Measurement" (MTM). This method is based on measuring the increased pressure which occurs in the system when the valve separating the lyophilisation chamber from the condenser is closed for a few moments. The condenser, or ice trap, is a component of the lyophilisation device, the walls of which are maintained at a low temperature by means of the circulation of a refrigerant fluid. The temperature difference between the product and the temperature at the condenser represents the driving force behind the sublimation process. The vapour released from the product sublimes on the chilled condenser walls, thus maintaining the level of vacuum within the system. By means of certain mathematical models proposed in the literature, it is possible to relate the dynamics of the pressure increase to the sublimation temperature. This method is non-invasive, but does have several drawbacks: the lyophilisation device must be equipped with a condenser outside the lyophilisation chamber, the separation valve closure time must be extremely small, and measurement cannot be performed continuously, hence it provides discontinuous monitoring of the sublimation temperature; furthermore, it provides the mean value of all the vials and does not allow assessment of the non-uniformity between the vials or ampoules placed in different areas of the lyophilisation device. During measurement, the temperature of the product has a tendency to increase, especially in the final phase of primary drying, thus exposing the product to risk of breakdown. It is also known that said method is not capable of providing accurate sublimation temperature values at the end of primary drying.

The following methods are currently available in relation to determining the state of progress of the primary drying phase:

1—insertion of thermocouples at various heights within the product container;

2—measuring of the mass of substance in the lyophilisation phase.

By means of the former method, when the sublimation front passes the temperature sensor, the temperature profile shows a sloping variation. In this way, by using various different thermocouples, it is possible to follow the temporal progression of the position of the moving interface. However, this method implies the use of a plurality of thermocouples inside the product, which have an influence on the mechanism of nucleation occurring during the freezing phase. For this reason, the measurements obtained this way cannot be considered as an absolute indication of the conditions prevailing in the non-monitored containers. Furthermore, for practical reasons, the simultaneous use of several thermocouples is limited to large sized containers only.

By means of the latter method it is indirectly deduced the position of the sublimation front inside the container knowing the initial mass of water in the solution, the dimensions of the container, and by measuring the mass of the substance. Of the various methods available for measuring mass, only those based on the use of special scales capable of operation under vacuum seem to disturb the process in a limited fashion, and hence, with appropriate contrivances, are the only methods capable of providing good results. Unfortunately, such scales are difficult to find, and are expensive.

An object of the present invention is that of allowing the realization of a system capable of determining the temperature profile and position of the sublimation front in real time during a lyophilisation process of substances contained in bottles, vials, small kegs, ampoules or similar containers.

SUMMARY OF THE INVENTION

These and other objects are achieved according to the invention by means of a system, whose main characteristics are defined in claim 1.

BRIEF DESCRIPTION OF THE DRAWINGS

Further characteristics and advantages of the invention will be apparent from the following detailed description, made purely by way of non-limiting example, with reference to the enclosed figures in which:

FIG. 1 is an overall outline of the measuring system according to the invention, FIG. 2 is a detail of two embodiments of the temperature sensor according to the invention.

DETAILED DESCRIPTION OF THE INVENTION

Figure 3:
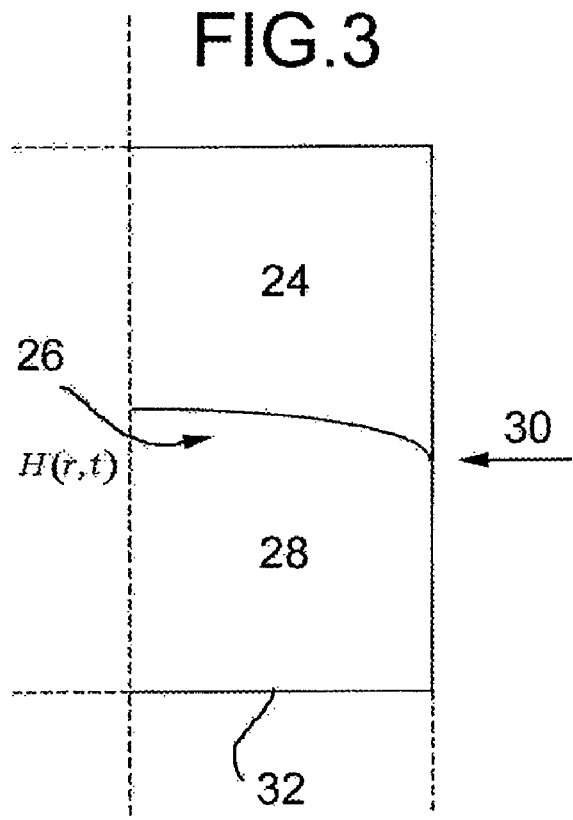
FIGS. 3 and 4 are schematic representations of a vial for a product undergoing lyophilisation, used for the definition of the process models.

FIG. 1 generally illustrates a system according to the invention, indicated by the number 2. Said system 2 comprises, for example, two bottles 4 containing the product to be lyophilised, a system for measuring the temperature 6, a wireless transmission system 8, capable of transmitting the measurements taken inside 10 the vacuum chamber of a lyophilisation system to the exterior 12 of said chamber, where said two environments are kept separate during the entire lyophilisation process. Furthermore, in the environment 12 there is a computer 16 with a system for processing and displaying the measurements, programmed to continuously calculate and provide an operator with the temperature of the product and the progress of the moving sublimation interface.

The temperature measuring system 6 has the following functions:
  measuring the temperature of the inner or outer walls, for example at the base of one or more bottles by means of temperature sensors, as shown in FIG. 2; for this reason, not just thermocouple sensors, but also active or passive, analogue or digital systems can be used.
  transmitting the results of the temperature measurement outside the lyophilisation chamber 12 by means of a radiofrequency system 8 comprising means of transmission inside the chamber and means of reception external to it. Finally, the measurements are sent to the processor 16 for processing and displaying of the results.

The measurement system 6 is powered autonomously by means of a battery inside the lyophilisation chamber, or from outside the chamber using radiofrequency signals.

FIG. 2 shows two example of embodiments of the temperature sensors. In the bottle indicated 4a the temperature sensor 20 is placed in contact with the inner wall of the base 22 of the bottle. In the bottle indicated 4b the temperature sensor 20 is placed in contact with the outer wall of the base 22 of the bottle. In this variant shown, the temperature sensors 20 are thermocouples.

The radiofrequency transmitter 8 located outside 12 the lyophilisation system is connected to the computer 16 by means of a serial connection. The measurement data transmitted to the computer 16, constituted by a single temperature measurement (internal or external) for each bottle being monitored (see FIG. 2), are processed by the processing and displaying system 16 capable of implementing a predetermined lyophilisation process model by means of a calculation algorithm based on the state observer concept (realization of a so-called software sensor).

The software sensor combines the physical temperature measurement of the container wall, for example at the base 22 of the container (process input) with a selected mathematical model, preferably simplified, of the process, and returns as output a series of physical process parameters, including, in particular, the spatial product temperature profile, the sublimation front position and the values of the process matter and heat exchange coefficients.

The Lyophilisation Process Models

The proposed device uses two different types of models, according to which the user selects to measure the container interior or exterior temperature.

There are many lyophilisation models known and used, mainly in applications in the food and pharmaceutical sectors. Even though some models have been developed for applications associated with the food sector, some of these have also been successfully applied to the lyophilisation of drugs.

During the primary drying phase, the most important parameter to be monitored and controlled is the product temperature. Indeed, primary drying should be carried out under controlled temperature conditions so as not to compromise the final product quality.

Another important variable which it might be useful to monitor is the position of the sublimation interface, the development of which determines the state of primary drying progress.

The transfer of matter through the product and the transfer of heat between the heating element (plate) and the product are a further two critical aspects which influence drying time. The transfer of matter depends on the temperature, the pressure conditions and the resistance of the dry structure to vapour flux. Heat transfer mainly depends on the composition and pressure of the gaseous phase in the lyophilisation chamber and the geometry of the container in the area in contact with the heating element (plate).

Prior art models have lead to the development of algorithms for simulating primary and secondary lyophilisation processes in containers such as vials and the like, under non-stationary conditions and with the assumption of two-dimensional geometry.

A diagram of a vial, considered cylindrical, is shown in FIG. 3. This figure shows only half of the vial since this approach assumes conditions of axial symmetry. Two distinct regions can be highlighted. Region 24 is a dry layer, which extends from the uppermost end of the vial to the sublimation interface 26. In the layer 24, the water has been essentially eliminated by means of sublimation, and partially by means of desorption, leaving a porous matrix through which the solvent (normally water vapour) is transported by means of diffusion and convection mechanisms. Region 28 consists of non-sublimed frozen solution.

During the primary drying phase, the moving interface 26, herein denoted by the function H(r,t), where t is the time and r is the distance from the central axis of the vial, recedes towards the base of the vial due to the sublimation of the product. If a heat flux $q_{side}$ is provided in a radial direction 30, as happens when there is irradiation from the chamber to the sides of the vial, the shape of the interface becomes curved.

It is necessary to emphasise that the irradiation of the vial is never uniformly distributed, and only a three-dimensional model could consider the different contribution originating from each individual angular position, with significantly increased complexity of the calculation algorithm. Hence, in the approach of the invention, the simplified assumption is made that the contribution of the irradiation is uniform along the perimeter of the vial, and under this assumption, the conditions of axial symmetry are still valid.

When the interface reaches the base of the vial, at the maximum radial position 32, it begins to contract and finally degenerates to a point in the centre of the base.

After the disappearance of the frozen layer 28—all the product is subjected to the secondary drying phase, which continues until the water residual content is reduced to the desired value.

The main assumptions made in developing this models are the following:

Thermal equilibrium between the gas passing through the dried layer and the porous solid: the temperature of the gas at any position is equal to the temperature of the dried material. This assumption allows a pseudo-homogeneous energy balance to be written for the gas/solid dry system, using effective parameters.

The moving interface is modelled as a mathematical surface, wherein there is no accumulation of matter and energy.

Water vapour and frozen water are considered to be in thermodynamic equilibrium at the sublimation interface.

The frozen region is homogeneous and contains a negligible portion of dissolved gas.

The water vapour and inert gas binary mixture which flows across the dried layer obeys the law of perfect gases, and this is justified by the very low pressure normally involved in the process.

The model equations describe the temporal and spatial development of the temperature of the dry layer 24, $T_I$, and of the frozen product 28, $T_{II}$. Heat is transferred across the frozen mass by conduction, and across the dry layer by means of convection and conduction.

The use of simulations has highlighted how the main effect of irradiation is the reduced primary drying time. However, even in the presence of irradiation, under the typical conditions in which the lyophilisation process is conducted in vials, only small radial gradients have been observed. Under such conditions, a one-dimensional model becomes a convenient alternative to the two-dimensional model.

It is possible that in some particular cases there may be pronounced radial effects, but because this occurs, the energy supplied to the vial must have a very strong component in the radial direction with respect to the axial direction, something which is normally not observed during lyophilisation in vials. Furthermore, this is considered to be an unwanted situation, since it can lead to dishomogeneity in the product and to the formation, during the sublimation process, of a frozen nucleus surrounded by product already dried.

Ultimately, the two-dimensional model of lyophilisation in vials is rather complex and its resolution has proved to be laborious and time consuming from the computational viewpoint. Hence, based on the previously discussed considerations, a simplification has been introduced into the invention which is based on the assumption of a null gradient along the radial coordinate, and this corresponds to follow a one-dimensional approach.

As it is known from the literature, various one-dimensional models have already been proposed, but none of them includes the heat exchange contribution derived from irradiation. Furthermore, the transfer of heat across the side walls of the vial has never been taken onto consideration even though it has been observed that this aspect can play an important role in the lyophilisation process in vials. For the aforementioned reasons, a novel one-dimensional model, introducing an energy balance describing the heat transfer across the glass of the vial, even in the presence of irradiation originating from the lyophilisation chamber, has been developed.

Figure 4:
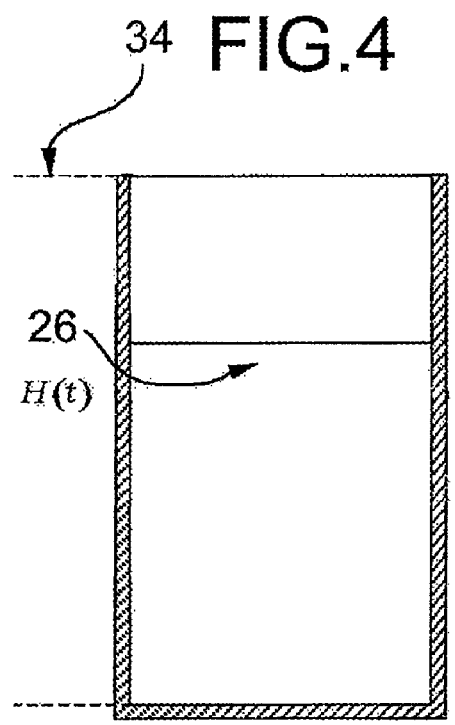

A diagram of the vial is shown in FIG. 4. The moving interface 26, always denoted H, is planar following the assumption of one-dimensional geometry. The origin of the z axis 34 is placed at the uppermost end of the vial. In detail, the complete model equations have been obtained by performing the balance of matter and energy for the dry layer, the balance of energy for the frozen layer and the balance of matter and heat across the sublimation interface. Finally, the balance of energy within the wall of the vial has been performed.

The complete model thus obtained is still rather complex due to the high number of variables and parameters considered and their interdependence. The synthesis of state observers based on this model is practically impossible, mainly due to the non-linearity of the problem, the difficulty in finding a suitable mathematical structure and the number and complexity of the mathematical manipulations involved.

Consequently, following the reduction of the dimensions of the problem from a two-dimensional problem to a one-dimensional problem, the one-dimensional model has been further simplified with the purpose of developing two reduced models capable of providing approximations, reasonably suitable for monitoring and controlling the process.

Reduced Model I

The first reduced model (hereinafter referred to as reduced model I) is a relatively simple model, and is obtained by performing a balance of energy for the frozen product and a balance of matter for the water vapour contained in the dried product, both considered under pseudo-stationary conditions, having hypothesised slow process dynamics.

The presence of inert gas and the transfer of heat across the walls of the vial are overlooked. The temperature at the bottom of the product is assumed to be physically measured variable of the process. In relation to the balance of matter, the starting point is the continuity equation for water vapour:

$$\frac{\partial}{\partial t}\left(\frac{p(z,t)}{T_I(z,t)}\right) = -\left[\frac{R}{\varepsilon M_W}\right]\frac{\partial}{\partial z}N_W(z,t) + \left[\frac{RK_d}{\varepsilon M_W}\right]\rho_{sW}(z,t) \quad (1)$$

wherein $0 < z < H(t)$, wherein $T_I$ is the temperature of the dry layer, p is the pressure, M is the molecular weight, R is the ideal gas constant, N is the mass flux, $\rho_{sw}$ is the mass concentration of absorbed water. The subscript w refers to the water vapour.

Said equation can be simplified by assuming pseudostationary conditions and overlooking the max flux due to deabsorbed water before the completion of the primary drying phase, giving:

$$\frac{\partial}{\partial z}N_W(z,t) \simeq 0 \quad (2)$$

Integration of equation 2 gives a constant value for the flux of vapour $N_w(t)$ along z, which can be resolved by referring to the constitutive equation for the transfer of mass in the dried layer:

$$N_W(z,t) = -\frac{Mk_1}{RT_I(z,t)}\frac{\partial}{\partial z}p_W(z,t) \quad (3)$$

wherein $k_1$ is the coefficient of effective diffusivity. Since $N_w(t)$ does not depend on z, it can be expressed as a function of the pressure drop across the dry layer:

$$N_W(t) = -\frac{M}{RT_i(t)}\frac{k_1}{H(t)}(p_{W,i}(t,T_i) - p_{W,c}(t)) \quad (4)$$

In the previous expression, $H(t)$ is the position of the moving sublimation front, $p_{w,i}$ is expressed as a function of $T_i$, the interface temperature, assuming ice-vapour equilibrium at the position $z=H(t)$, and $p_{w,c}$ is the vapour pressure at the peak of the dry product, at position $z=0$, considered to be equal to the partial pressure of water in the chamber. The mean dry layer temperature value has been approximated with the value of the interface temperature $T_i$.

Finally, the balance of matter at the interface is introduced, providing the dynamic progress of $H(t)$:

$$\frac{dH}{dt} = -\frac{1}{\rho_{II} - \rho_{Ie}}N_W(t) \quad (5)$$

where the subscript II refers to the frozen layer and the subscript I refers to the dry layer.

In relation to the balance of energy for the frozen layer, by ignoring the exchange of heat with the walls of the vial, one obtains:

$$k_{II}\frac{\partial^2}{\partial z^2}T_{II}(z,t) = 0 \quad (6)$$

This equation can be easily integrated in space to give an expression for the heat flux $q(t)$, which is itself also constant along z:

$$q(t) = -k_{II}\frac{\partial}{\partial z}T_{II}(z,t) \quad (7)$$

By performing a second integration between the generic position z and the base of the vial, assumed to have length equal to L, a linear temperature profile $T_{II}$ is obtained which depends on the time through the heat flux and the temperature at the base of the frozen product $T_B$:

$$T_{II}(z,t) = \frac{q(t)}{k_{II}}\cdot(z-L) + T_B(t) \quad (8)$$

The temperature at the sublimation interface is obtained from equation 8 by substituting $z=H(t)$:

$$T_i(t) = \frac{q(t)}{k_{II}}\cdot(H(t)-L) + T_B(t) \quad (9)$$

In order to resolve the system of equations of the reduced model I it is necessary to apply the conditions to the boundary defining the flux of heat across the frozen layer.

The flux at the base of the vial is expressed by the equation:

$$q(t) = K_v(T_{plate}(t) - T_B(t)) \quad (10)$$

wherein the heat exchange coefficient $K_v$ includes the resistance to the transfer of heat across the base of the vial of thickness $\delta$, and $T_{plate}$ is the temperature of the heating element (plate). At the moving interface, it is assumed that the heat flux is due solely to the sublimation of the ice, giving:

$$q(t) = -\Delta H_s N_w(t) \quad (11)$$

wherein $\Delta H_s$ is the enthalpy of sublimation.

By reorganising equations 4, 5, 9, 10 and 11 and eliminating the expression of heat flux $q(t)$ and mass flux $N_w(t)$ the final form of the reduced model is obtained, given by the following equations:

$$\frac{dH}{dt} = \frac{1}{\rho_{II} - \rho_{Ie}}\frac{M}{RT_i}\frac{k_1}{H}(p_{w,i}(T_i) - p_{w,c}) \quad (12)$$

$$\left(\frac{1}{K_v} + \frac{L-H}{k_{II}}\right)^{-1}(T_{plate} - T_i) = \frac{\Delta H_s M}{RT_i}\frac{k_1}{H}(p_{w,i}(T_i) - p_{w,c}) \quad (13)$$

$$T_{II,b} = T_{plate} - \frac{1}{K_v}\left(\frac{1}{K_v} + \frac{L-H}{k_{II}}\right)^{-1}(T_{plate} - T_i) \quad (14)$$

The final equation connects the temperature and the interface position with the temperature measured at the base of the vial, while non-linear equation 13 provides a relationship between $T_i$ and H. The key parameters of the model are the matter transfer and heat transfer coefficients.

The proposed model is a simplified model, since heat transfer in the dry state is not considered and energy transport in the frozen layer occurs under pseudo-stationary conditions, an approximation from which it is derived that all the energy transferred to the product is used for sublimation. Furthermore, the walls of the vial are assumed to be screened from the irradiation. It should be observed that in the complete model of the process, the energy originating from the heat plate is mainly transferred to the product across the base of the container, but is also partly transferred across the walls of the vial, as a consequence of the conduction across the glass. In the reduced model being the object of the invention, the presence of the vial is not considered and the energy originating from the heat plate only reaches the base of the product. Under such conditions, so that the reduced model gives the same results as the detailed model of the process, it is necessary to use an effective heat transfer coefficient, which includes the effect of heat conduction along the vial and irradiation, if present.

As developed, the pseudostationary type model is similar to the URIF model described in the articles by Sandall, O. C., King, C. J., Wilke, C. R., "The Relationship Between Transport Properties and Rates of Freeze-Drying of Poultry Meat" in *AIChE Journal*, 1967, vol. 13(4), pp. 428-438 and Hill, J. E., Sunderland, J. E. "Sublimation-dehydration in the continuum, transition and free-molecule flow regimes", in *Int. J Heat and Mass Transfer*, 1971, vol. 14, pp. 625-638.

However, the known model and the variants thereof assume constant temperature at the base of the vial, while the model presented here considers $T_B$ as the variable being measured, which is bound to the key process parameters by means of equation 14.

Measurement of $T_B$ is fundamentally important for the development of estimation strategies based on use of the reduced model.

Reduced Model II

The second reduced model, (hereinafter: reduced model II) is more complex with respect to the previously described model. Heat transfer is considered both across the frozen and dry layers, and across the vial walls, while matter transfer is modelled as per the previous model. The contribution of irradiation is not considered directly, and any effect is incorporated in the effective coefficient of heat transfer. Furthermore, the assumption of pseudostationary conditions allows the attainment of an analytical solution to the problem in the spatial domain.

By adopting the same assumptions made in the previous section, the flux of vapour in the dry layer, assumed to be constant along z, and the progress of the moving sublimation interface over time, can be expressed as follows:

$$N_W(t) = -\frac{M}{RT_i(t)} \frac{k_1}{H(t)} (p_{w,i}(t, T_i) - p_{w,c}(t)) \quad (15)$$

$$\frac{dH}{dt} = -\frac{1}{\rho_{II} - \rho_{Ie}} N_W(t) \quad (16)$$

Said equations are combined to give the following equations:

$$\frac{dH}{dt} = \frac{1}{\rho_{II} - \rho_{Ie}} \frac{M}{RT_i} \frac{k_1}{H} (p_{w,i}(T_i) - p_{w,c}) \quad (17)$$

Disregarding the accumulation term and the effects due to the water desorption linked to the energy balance for the dry layer gives:

$$\frac{\partial^2 T_I}{\partial z^2} - \left[\frac{2}{R_G^2}\right](T_I - T_{I,gl}) = 0 \quad (18)$$

wherein the subscript gl refers to the material (glass) of the vial.

With regard to the balance of energy in the part of the vial in contact with the dry layer, the following equation can be obtained:

$$\frac{\partial^2 T_{I,gl}}{\partial z^2} + \left[\frac{2k_{Ie}}{\lambda_{gl}(R_{G,e}^2 - R_{G,i}^2)}\right](T_I - T_{I,gl}) = 0 \quad (19)$$

wherein $\lambda$ is the thermal conductance of the vial.

In the same way, it is possible to assume pseudostationary conditions for the frozen product and for the part of the glass of the vial in contact with the ice, obtaining the following equations:

$$\frac{\partial^2 T_{II}}{\partial z^2} - \left[\frac{2}{R_G^2}\right](T_{II} - T_{II,gl}) = 0 \quad (20)$$

$$\frac{\partial^2 T_{II,gl}}{\partial z^2} + \left[\frac{2k_{II}}{\lambda_{gl}(R_{G,e}^2 - R_{G,i}^2)}\right](T_{II} - T_{II,gl}) = 0 \quad (21)$$

wherein $C_P$ is the specific heat at constant pressure.

The system of homogeneous, second order linear differential equations given by (18)-(21) may be resolved analytically, to give the temperature profile in the product and in the vial, along the axial coordinate, for any given moment in time. The solution of the system is as follows:

$$T_I = -2(1-a_I)C_3 \cos h(\alpha_I H \xi) + a_I C_6 \quad (22)$$

$$T_{I,gl} = 2a_I C_3 \cos h(\alpha_I H \xi) + a_I C_6 \quad (23)$$

$$T_{II} = -(1-a_{II})(C_1 e^{-\alpha_{II}(L-H)\vartheta} + C_2 e^{\alpha_{II}(L-H)\vartheta}) + a_{II}(C_4 \vartheta + C_5) \quad (24)$$

$$T_{II,gl} = a_{II}(C_1 e^{-\alpha_{II}(L-H)\vartheta} C_2 e^{\alpha_{II}(L-H)\vartheta}) + a_{II}(C_4 \vartheta + C_5) \quad (25)$$

wherein $C_1$-$C_6$ are the integration constants. The expressions of the parameters appearing in the system are reported in the table below:

$$\xi = \frac{z}{H}$$

$$\alpha_I = \left[1 + \frac{\lambda_{gl}(R_{G,e}^2 - R_{G,i}^2)}{k_{Ie} R_{G,i}^2}\right]^{-1}$$

$$\alpha_I = \left[\frac{2k_{Ie}}{\lambda_{gl}(R_{G,e}^2 - R_{G,i}^2)} + \frac{2}{R_{G,i}^2}\right]^{1/2}$$

$$\vartheta = \frac{z-H}{L-H}$$

$$\alpha_{II} = \left[1 + \frac{\lambda_{gl}(R_{G,e}^2 - R_{G,i}^2)}{k_{II} R_{G,i}^2}\right]^{-1}$$

$$\alpha_{II} = \left[\frac{2k_{II}}{\lambda_{gl}(R_{G,e}^2 - R_{G,i}^2)} + \frac{2}{R_{G,i}^2}\right]^{1/2}$$

$$c_{II} = \frac{K_v}{k_{II}}$$

$$c_{II,gl} = \frac{K_v}{\lambda_{gl}}$$

$$b_2 = \frac{\Delta H_s M}{RT_i} \frac{k_1}{k_{II}} \frac{(p_{w,i}(T_i) - p_{w,c})}{H}$$

With the purpose of determining the expressions of the integration constants, appropriate conditions must be applied to the boundary, expressing the continuity of the temperature profile of the product and the glass at the interface and defining the heat flux at the base of the vial and at the sublimation interface:

$$\xi = 1, \vartheta = 0 \qquad T_I |_{\xi=1} = T_{II} |_{\vartheta=0}$$

$$\xi = 1, \vartheta = 0 \qquad T_{I,gl} |_{\xi=1} = T_{II,gl} |_{\vartheta=0}$$

$$\xi = 1, \vartheta = 0 \qquad \frac{k_{II}}{L-H} \frac{\partial T_{II}}{\partial \vartheta}\bigg|_{\vartheta=0} = \frac{\Delta H_s M}{RT_i} \frac{k_1}{H}(p_{w,i}(T_i) - p_{w,c})$$

$$\xi = 1, \vartheta = 0 \qquad \frac{\partial T_{I,gl}}{\partial \vartheta}\bigg|_{\xi=1} = \frac{H}{L-H} \frac{\partial T_{II,gl}}{\partial \vartheta}\bigg|_{\vartheta=0}$$

-continued $$\vartheta = 1 \qquad \frac{k_{II}}{L-H}\frac{\partial T_{II}}{\partial \vartheta}\bigg|_{\vartheta=1} = K_v(T_{plate} - T_{II}\vert_{\vartheta=1})$$

$$\vartheta = 1 \qquad \frac{\lambda_{gl}}{L-H}\frac{\partial T_{II,gl}}{\partial \vartheta}\bigg|_{\vartheta=1} = K_v(T_{plate} - T_{II,gl}\vert_{\vartheta=1})$$

By applying the aforementioned conditions to the boundary, the following system, linear in $C_1$-$C_6$, is obtained:

$$C_1 + C_2 - C_3\left[2\frac{a_I}{a_{II}}\cosh(\alpha_I H)\right] + C_5 - C_6\left(\frac{a_I}{a_{II}}\right) = 0 \tag{26}$$

$$C_1 - C_2 + C_3\left[2\frac{a_I\alpha_I}{a_{II}\alpha_I}\frac{L-H}{H}\sinh(\alpha_I H)\right] - C_4\left(\frac{1}{a_{II}}\right) = 0 \tag{27}$$

$$C_1\left(\frac{c_{II,gl} - \alpha_{II}}{c_{II,gl}}e^{-\alpha_{II}(L-H)}\right) + \tag{28}$$
$$C_2\left(\frac{c_{II,gl} + \alpha_{II}}{c_{II,gl}}e^{\alpha_{II}(L-H)}\right) + C_4\left(\frac{L-H+c_{II,gl}}{c_{II,gl}}\right) + C_5 = \frac{T_{plate}}{a_{II}}$$

$$C_1\left(-\frac{c_{II} - \alpha_{II}}{c_{II}}e^{-\alpha_{II}(L-H)}\right) + \tag{29}$$
$$C_2\left(\frac{c_{II} + \alpha_{II}}{c_{II}}e^{\alpha_{II}(L-H)}\right) + C_4\left(1 + \frac{1}{c_{II}(L-H)}\right) + C_5 = \frac{T_{plate}}{a_{II}}$$

$$C_1 - C_2 + C_4\left(\frac{1}{\alpha_{II}(L-H)}\frac{a_{II}}{1-a_{II}}\right) = \frac{b_2}{\alpha_{II}(L-H)} \tag{30}$$

$$C_1 + C_2 - C_3\left[2\frac{1-a_I}{1-a_{II}}\cosh(\alpha_I H)\right] - C_5\left(\frac{a_{II}}{1-a_{II}}\right) + C_6\left(\frac{a_I}{1-a_{II}}\right) = 0 \tag{31}$$

Once the system (26)-(31) is resolved, the integration constants may be substituted in the equations to give the temperature profile in the product and in the vial, in particular:

$$T_i = -(1-a_{II})(C_1+C_2) + a_{II}C_5 \tag{32}$$

$$T_{B,gl} = +a_{II}(C_1 e^{-\alpha_{II}(L-H)} + C_2 e^{\alpha_{II}(L-H)} + C_4 + C_5) \tag{33}$$

The non-linear equation (32) relates the temperature at the interface with the position of the moving sublimation front, since $C_1$, $C_2$, $C_5$ are dependent on $T_i$ and $H$; the equation (33) allows expressing the temperature of the glass at the base of the vial as a function of $T_i$ and $H$.

The analytical expressions of the integration constants are as follows:

$$C_1 = \frac{b_2\cdot\left(-a_1\alpha_1\tanh(\alpha_1 H)\cdot\frac{1}{a_{II}} - R_2 e^{\alpha_{II}(L-H)} + \alpha_{II}\right)}{A_1\alpha_I\tanh(\alpha_I H)\cdot\left(-2\frac{1-a_{II}}{a_{II}}\alpha_{II} + R_1 e^{-\alpha_{II}(L-H)} - R_2 e^{\alpha_{II}(L-H)}\right) - \alpha_{II}(R_1 e^{-\alpha_{II}(L-H)} + R_2 e^{\alpha_{II}(L-H)})}$$

$$C_2 = \frac{b_2\cdot\left(a_1\alpha_1\tanh(\alpha_1 H)\cdot\frac{1}{a_{II}} - R_2 e^{\alpha_{II}(L-H)} + \alpha_{II}\right)}{A_1\alpha_I\tanh(\alpha_I H)\cdot\left(-2\frac{1-a_{II}}{a_{II}}\alpha_{II} + R_1 e^{-\alpha_{II}(L-H)} - R_2 e^{\alpha_{II}(L-H)}\right) - \alpha_{II}(R_1 e^{-\alpha_{II}(L-H)} + R_2 e^{\alpha_{II}(L-H)})}$$

$$C_3 = \frac{1}{2\cosh\alpha_I}(C_1 + C_2)$$

$$C_4 = \left[\frac{b_2}{a_{II}} - \left(\frac{1-a_{II}}{a_{II}}\right)\alpha_{II}(C_1 - C_2)\right](L-H)$$

$$C_5 = \frac{T_{plate}}{a_{II}} - C_1\left(\frac{c_{II,gl} - \alpha_{II}}{c_{II,gl}}\right)e^{-\alpha_{II}(L-H)} - C_2\left(\frac{c_{II,gl} + \alpha_{II}}{c_{II,gl}}\right)e^{\alpha_{II}(L-H)} - \frac{C_4}{L-H}\left(\frac{c_{II,gl} + 1}{c_{II,gl}}\right)$$

$$C_6 = \frac{a_{II}}{a_I}(C_1 + C_2 + C_5) - 2C_3\cosh\alpha_1$$

wherein $$R_1 = \alpha_{II} - \left(\frac{c_{II} - \alpha_{II}}{c_{II,gl} - c_{II}}\right)\left(\frac{c_{II,gl}}{\alpha_{II}}\right) \text{ and}$$

$$R_2 = \alpha_{II} + \left(\frac{c_{II} + \alpha_{II}}{c_{II,gl} - c_{II}}\right)\left(\frac{c_{II,gl}}{\alpha_{II}}\right)$$

The reduced model presented in this section is derived formally from the complete model; both the energy transfer in the product and along the glass of the vial are modelled. The simplification introduced by the assumption of a pseudostationary state allows analytically resolving one part of the problem, leading to expressing the axial temperature profile along the product and along the vial by means of non-linear algebraic equations.

Once more, the reduced complexity of the problem is significantly important for the development of monitoring and control techniques based on the model.

Despite the approximations adopted in developing reduced model II, the comparison with the complete model is very good. Indeed, the development over time of the temperature at the interface and the base of the vial and the position of the moving front obtained by means of the simulation of the two models are practically overlapping. It should be observed that in this case, both in the simulations with the complete model and in the simulations with the reduced model, the same heat transfer coefficient value has been adopted. Indeed, since in the equations of reduced model II, the effect of the heat exchange between the glass of the vial and the product is correctly modelled, it has not been necessary to make any corrections to the heat transfer coefficient in order to make the predictions of the complete model coincide with that of the reduced model. Furthermore, reduced model II gave an optimal estimate of the axial temperature profile.

Figure 5:
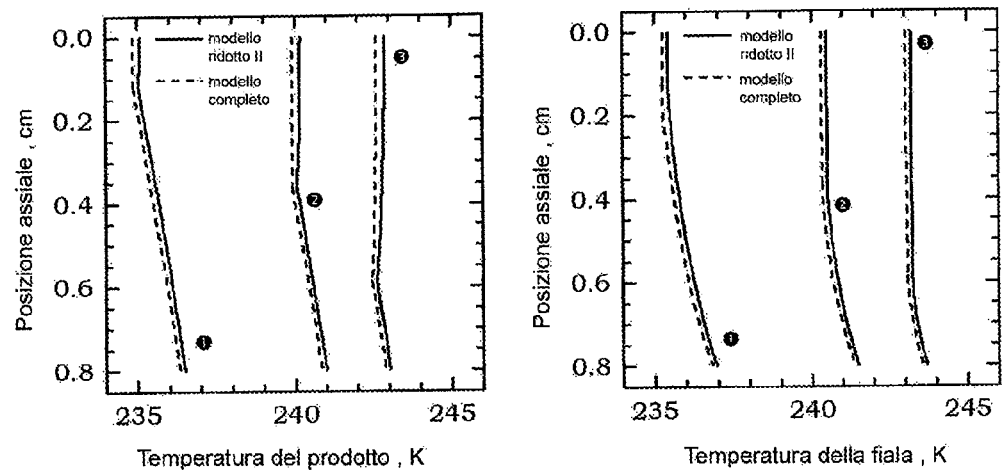
FIG. 5 shows two graphs comparing the temperature profile of the product and the vial, between reduced model II and the complete model, for a lyophilisation process.

FIG. 5 shows the temperature profile of the product and the vial along the axial coordinates, at three different times during primary drying, and it can be observed how the differences between the estimates of the two models are very small and, in any case, always of the order of 0.1 K.

The State Observers

Starting from the two reduced models presented in the previous sections, some mathematical methods have been processed which can be used with the purpose of estimating the temperature, position of the sublimation interface, the value of the matter transfer coefficient and the heat transfer coefficient during the process. In particular, a first method based on the state observers (the so-called software sensors) has been developed to estimate the temperature of the product by means of the combination of simplified theoretical models (reduced model I) and a single product temperature measurement.

However, an important objective of optimisation of the lyophilisation process is that of minimising human intervention, avoiding disturbing the process with invasive methods. This can be obtained by means of the development of an accurate and robust procedure for determining the temperature of the product without using physical sensors inserted inside the vial. For this purpose, another type of software-sensor has been synthesised that is capable of estimating the dynamics of the product temperature starting from reduced model II and performing a single temperature measurement outside the vial, i.e. by means of sensors that are not in direct contact with the product.

Many modern dynamic system control theories are actually based on a representation of the process in the state space. This representation allows the description of the behaviour of the system by means of the variation of its state. The state of a system can be defined as the minimum of information necessary to completely describe the system at any given moment in time.

Thus, the dynamic of a system is defined by the following collection of differential equations:

$$\dot{x}=f(x,u) \quad (34)$$

where x, belonging to the collection of natural real numbers, is the state of the system, $u \in R^m$ and is the vector of the control variables, f is an application of $R^n \times R^m$ in $R^n$ which gives rise to the derivative of the state dependent on the state itself and on the law of control u applied to the system.

By starting from the basic postulate that the state $x \in R^n$ is known unambiguously, these theories allow the law of control to be calculated:

$$u(t)=K(x(t),p(t)) \quad (35)$$

wherein $p(t) \in R^p$ is the value of a given number of links to instant t and K is an application of $R^n \times R^p$ in $R^m$.

Application of the law of control requires knowledge of the state variables vector. In many cases, as a result of cost considerations and physical constraints, the number and type of sensors that can be applied for measuring the value of the state variables can be very limited, and in such cases it is necessary to resort to the calculation (estimate) provided by state observers. The observer combines the a priori knowledge of the physical system (the mathematical model) with the experimental data (the physical measurements) to provide an estimate of the state and the process parameters.

Synthesis of the observers for non-linear systems is generally very difficult.

Among the main mathematical tools which can be used, one of the best known and frequently used is the Kalman filter. Said filter is essentially a set of mathematical equations which implement a predictor-corrector type observer, which minimises the estimated error covariance, under predefined conditions.

The application being the object of the invention is preceded by the synthesis of an extended Kalman type observer for each of the previously illustrated reduced models I and II. The observer estimates the dynamic of the temperature at the interface $T_i$ at each time point during the primary drying phase, using the temperature at the base of the frozen product $T_B$ as the measured variable.

The numerical difficulties involved in designing an observer based on an extended Kalman filter make estimation very laborious from the computational viewpoint. Alternatively, a different approach, consisting in the development of a high gain observer, can be used. The calculations involved in determining the gain of the proposed observers does not require the resolution of any differential equations, and their calibration is very simple.

The State Observers for Reduced Model I

In designing the state observers for reduced model I the effective diffusion coefficient of the dry layer $k_1$, which has an influence on mass transfer, and the heat transfer coefficient between the heat plate and the base of the vial, $K_v$, are considered unknown parameters and are themselves estimated, together with the interface temperature $T_i$. By knowing $T_i$, $K_v$, and $k_1$, the position of the interface may be calculated by means of equation (13).

The equations describing reduced model I are reported here for reasons of clarity:

$$\frac{dH}{dt} = \frac{1}{\rho_{II} - \rho_{Ie}} \frac{M}{RT_i} \frac{k_1}{H}(p_{w,i}(T_i) - p_{w,c}) \quad (12)$$

$$\left(\frac{1}{K_v} + \frac{L-H}{k_{II}}\right)^{-1}(T_{plate} - T_i) = \frac{\Delta H_s M}{RT_i} \frac{k_1}{H}(p_{w,i}(T_i) - p_{w,c}) \quad (13)$$

$$T_{II,b} = T_{plate} - \frac{1}{K_v}\left(\frac{1}{K_v} + \frac{L-H}{k_{II}}\right)^{-1}(T_{plate} - T_i) \quad (14)$$

With the purpose of developing an observer for said model, the system must be expressed in terms of state variables in the following form:

$$\dot{x}=f(x,u)$$

$$y=h(x,u)$$

Since it is proposed to estimate the dynamic of the interface temperature $T_i$, the diffusion coefficient $k_1$ and the coefficient of heat transfer at the base of the vial $K_v$, the process state vector may be defined as:

$$x=(x_1,x_2,x_3)^T=(T_i,K_v,k_1)^T. \quad (36)$$

The observer may be provided using the temperature of the product as a physical measurement y measured at any axial position z and given by equation (8).

$$T_{II}(z,t) = \frac{K_v(T_{plate}(t) - T_B(t))}{k_{II}}(z-L) + T_B(t) \quad (8)$$

By way of example, below are reported the equations of an observer using the temperature measurement $T_B$ at the base of the frozen product (z=L) as state equation, expressed as:

$$y=h(x_1,x_2,x_3,u)=T_B(T_i,K_v,k_1,T_{plate}) \quad (37)$$

wherein the temperature of the heating plate $T_{plate}$ is considered as the manipulable input of the process.

Hence, the process dynamic may be defined by the following system of equations:

$$\dot{x} = \begin{pmatrix} x_1 \\ x_2 \\ x_3 \end{pmatrix} \quad (38)$$

$$= \begin{pmatrix} \frac{dx_1}{dt} \\ \frac{dx_2}{dt} \\ \frac{dx_3}{dt} \end{pmatrix}$$

$$= \begin{pmatrix} f_1(x_1,x_2,x_3,u) \\ 0 \\ 0 \end{pmatrix}$$

$$= f(x,u)$$

wherein the derivatives of $x_2=K_v$ and $x_3=k_1$ are set equal to zero because said quantities are considered to be constant during the process. In this approach, it is assumed that the observer may compensate for the variations in $K_v$ and $k_1$ through the action of correction terms of the dynamic of the estimated state $K(t)(\hat{y}-y)$ (refer to equation 43).

The dynamic equation of reduced model I only gives the progress of the position of the moving sublimation front H, but the shape of the system 38 requires an expression for the derivative of $x_1 = T_i$ with respect to time. This may be calculated by differentiating the function $H=H(T_i, K_v, k_1, T_{plate})=H(x,u)$ with respect to time, to give:

$$\frac{dH}{dt} = \frac{\partial H}{\partial x_1}\frac{dx_1}{dt} + \frac{\partial H}{\partial x_2}\underbrace{\frac{dx_2}{dt}}_{=0} + \frac{\partial H}{\partial x_3}\underbrace{\frac{dx_3}{dt}}_{=0} + \frac{\partial H}{\partial u}\frac{du}{dt} \qquad (39)$$

$$\Rightarrow \frac{dx_1}{dt} = \left(\frac{dH}{dt} - \frac{\partial H}{\partial u}\frac{du}{dt}\right)\left(\frac{\partial H}{\partial x_1}\right)^{-1}$$

It follows from the aforementioned equation that the determination of the expression of $dx_1/dt$ requires knowledge of the partial derivative of H with respect to $x_1$. By rearranging equation (13) it is possible to obtain the following expression of H as a function of the state:

$$H = \frac{\alpha\gamma}{\alpha + \beta} \qquad$$

wherein the following substitutions have been performed:

$$\alpha = \alpha(x_1, x_3)$$
$$= \frac{\Delta H_s M}{R}\frac{x_3}{x_1}(p_{w,i}(x_1) - p_{w,c})$$
$$\beta = \beta(x_1, u)$$
$$= k_{II}(u - x_1)$$
$$\gamma = \gamma(x_2)$$
$$= \frac{k_{II}}{x_2} + L$$
$$u = T_{plate}$$
$$\delta = \frac{\Delta H_s}{\rho_{II} - \rho_I}$$

Starting from the above equation, it is possible to calculate the expressions for $dH/dt$, $\partial H/\partial x_1$ and $\partial H/\partial u$.

The combination of the three equations thus calculated gives the dynamic development of the temperature at the interface $x_1 = T_i$:

$$\frac{dx_1}{dt} = \left[\delta \cdot \frac{(\alpha + \beta)^3}{\gamma^2} + \alpha\frac{d\beta}{du}\frac{du}{dt}\right]\frac{1}{\beta\frac{\partial\alpha}{\partial x_1} - \frac{d\beta}{dx_1}\alpha} \qquad (40)$$

$$= f_1(x_1, x_2, x_3, u)$$

wherein the equation of the measurement (14) may be rewritten in terms of state and space variables according to the equation:

$$y = u - \frac{\alpha + \beta}{x_2\gamma} \qquad (41)$$
$$= h(x_1, x_2, x_3, u)$$

Using the previous notation, the equations given by the reduced model I may be expressed in the space of the states by means of the system (42):

$$\dot{x} = \begin{pmatrix} \left[\delta \cdot \frac{(\alpha + \beta)^3}{\gamma^2} + \alpha\frac{d\beta}{du}\frac{du}{dt}\right]\frac{1}{\beta\frac{\partial\alpha}{\partial x_1} - \frac{d\beta}{dx_1}\alpha} \\ 0 \\ 0 \end{pmatrix} \qquad (42)$$

$$= f(x, u)$$

$$y = u - \frac{\alpha + \beta}{x_2\gamma}$$
$$= h(x, u)$$

The general structure of an extended Kalman observer for a system set in form (42) is given by the following equations:

$$\dot{\hat{x}} = f(\hat{x}, u) + K(t)(\hat{y} - y) \qquad (43)$$

$$\hat{y} = h(\hat{x}, u) \qquad (44)$$

$$K(t) = S^{-1}(t)\left(\frac{\partial h}{\partial x}\bigg|_{\hat{x}}\right)^T \qquad (45)$$

$$\dot{S}(t) = -\left(\frac{\partial f}{\partial x}\bigg|_{\hat{x}}\right)^T S(t) - S(t)\frac{\partial f}{\partial x}\bigg|_{\hat{x}} + \left(\frac{\partial h}{\partial x}\bigg|_{\hat{x}}\right)^T\frac{\partial h}{\partial x}\bigg|_{\hat{x}} - S(t)\Lambda S(t) \qquad (46)$$

Figure 6:
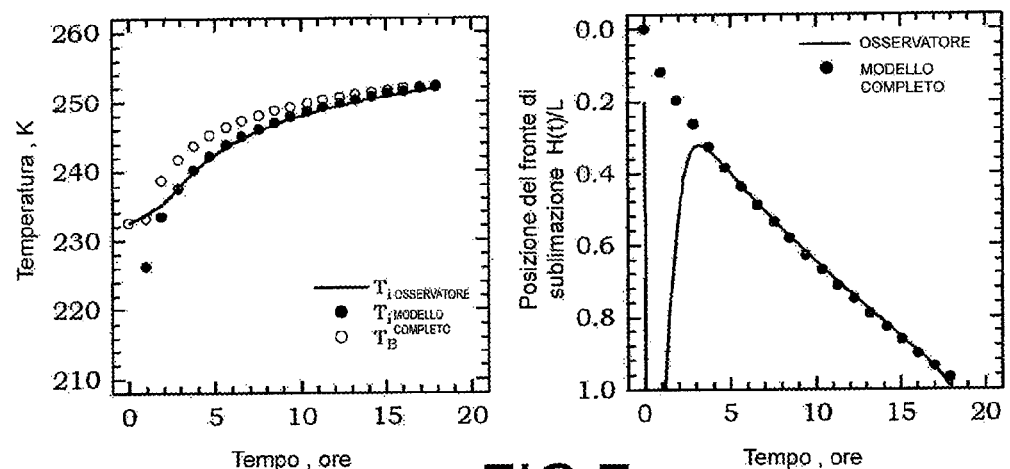
FIG. 6 shows two graphs comparing the predictions of the Kalman state observer, for reduced model I, and the values provided by the detailed model of the process.

FIG. 6 (left hand side) shows a comparison of the predictions provided by the observer, with the temperature at the interface and the base of the product simulated by means of the detailed process model. The right hand side of the figure shows the development of the moving sublimation front over time. The parameters used in the complete model simulations are:

$K_v$: 29.1 [$Wm^{-2}K^{-1}$]

$k_1$: 2.97 ($\times 10^{-3}$)[$m^2s^{-1}$].

The extended Kalman filter requires the solution of the Riccati dynamic equation (equation (46)) making it laborious from the viewpoint of computation time. To overcome this drawback, a high gain observer has been realized which does not require an additional dynamic equation in its formulation for the solution of the estimation problem.

The synthesis of a high gain observer starting from the representation in terms of state variables given by the system (42) would require the evaluation of the third derivative of $y=h(x)$ and the mixed second derivative of $f_1$. Given the complexity of the functions involved, it has been preferred to precede the problem of estimation by means of the observer with a non-linear regression procedure. Said procedure is used to estimate the values of $K_v$ and $k_1$ by minimising, in the sense of least squares, the difference between the temperature values $T_B$ provided by reduced model I and the measurement of the temperature at the base of the product obtained during the initial primary drying phase. Subsequently, the real time estimation process may be started using the high gain observer described below, wherein the value of $k_1$ obtained by regression is assumed as the known parameter allowing the reduction of the dimensions of the problem from $R_3$ to $R_2$.

At this point, the state space representation of reduced model I with $x \in R^2$ may be obtained by taking the system (42) and eliminating the equation relating to $x_3 = k_1$:

$$\dot{x} = \left( \left[ \delta \cdot \frac{(\alpha+\beta)^3}{\gamma^2} + \alpha \frac{d\beta}{du}\frac{du}{dt} \right] \frac{1}{\beta \frac{\partial \alpha}{\partial x_1} - \frac{d\beta}{dx_1}\alpha} \right) \quad (47)$$

$$= \begin{pmatrix} f_1(x_1, x_2, u) \\ 0 \end{pmatrix}$$

$$= f(x,u)$$

$$y = u - \frac{\alpha+\beta}{x_2 \gamma}$$

$$= h(x, u)$$

A high gain observer for this system may be expressed as follows:

$$\dot{\hat{x}} = f(\hat{x}, u) - \left( \frac{\partial \Phi_t}{\partial x} \bigg|_{\hat{x}} \right)^{-1} S_\theta^{-1} C^T (\hat{y} - y)$$

$$\hat{y} = h(x, u)$$

wherein the gain of the observer is given by $S_\theta^{-1}C^T = (2\theta \; \theta^2)^T$ and the transformation vector $\Phi_t(x)$ has the following expression:

$$\Phi_t(x) = \begin{pmatrix} h(x, u) \\ \frac{\partial h}{\partial x_1} f_1(x, u) + \frac{\partial h}{\partial u}\frac{\partial u}{\partial t} \end{pmatrix} \quad (48)$$

It may be observed that the reduction of the order of the system from $R^3$ to $R^2$ simplifies the problem for two reasons: firstly because of the need to integrate just two dynamic equations instead of three, and also because just the second derivative of h with respect to $x_1$, $x_2$, u and the first derivative of $f_1$ are necessary to calculate the correction terms of the dynamic of the observer.

Figure 7:
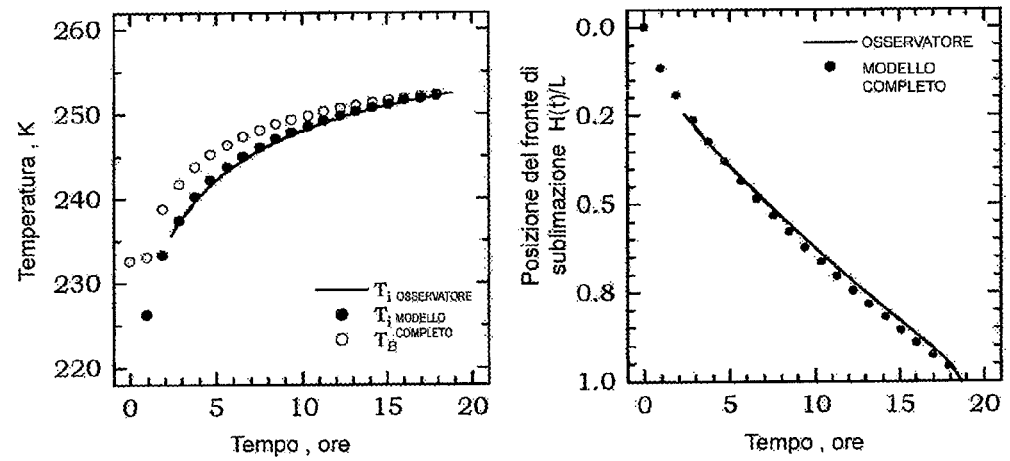
FIG. 7 shows two graphs comparing the predictions of the high gain state observer, for reduced model I, and the values provided by the detailed model of the process.

FIG. 7 reports the results of the simulations performed with the synthesised high gain observer, using the same values used in FIG. 6 for parameters $K_v$ and $k_1$.

The State Observers for Reduced Model II

A Kalman observer has also been developed for the reduced model II. The variables and parameters considered in the design of said observer are again the temperature and the position of the moving interface, and the heat and matter transfer parameters. With respect to the previously developed observer, the difference is the measured variable, in that here, the use of the vial wall external temperature has been selected. This is possible since the equations of the reduced model II allow the expression of the vial temperature, for example at the base of the container, as a function of the variables to be observed, i.e. the state of the system.

The use of the container outer wall temperature measurement allows non-invasive monitoring of the process, thus overcoming the drawbacks associated with the use of the invasive measurement systems described in the preamble.

In order to synthesise an observer for the reduced model II it is necessary to start from the set of equations defining the model, in which the terms $C_1$-$C_6$, and non-linear functions of $T_i$, H, $K_v$ and $k_1$ appear. In the development of the observer, it is assumed that the state of the system consists of H, $K_v$ and $k_1$. Consequently, we have:

$$x = (x_1 x_2 x_3)^T = (H \; K_v \; k_1)T \quad (49)$$

The observer may be realized using the container exterior temperature measured at any axial position z and given by equation (23) or (25) as a physical measurement. By way of example, below are reported the equations of an observer using the temperature of the base of the vial as measurement state equation:

$$y = h(x_1, x_2, x_3, u) = T_{B,gl}(H, K_v, k_1, T_{plate}) \quad (50)$$

It may be observed that in this approach, the temperature at the interface is not considered to be a state of the system, but is assumed to be a function of the state according to implicit equation (32). In terms of variables of state, equation (32) is:

$$\Psi(T_i, x, u) = T_i + (1-a_{II})(C_1(T_i, x) + C_2(T_i, x)) - a_{II}C_5(T_i, x, u) = 0 \quad (51)$$

wherein the expression of the constants must be determined analytically as a function of $T_i$ and x by means of the solution of the linear system (26-31).

At the light of the previous considerations, the equations of reduced model II may be rewritten as follows:

$$\dot{x} = \begin{pmatrix} \frac{1}{\rho_{II}-\rho_1}\frac{M}{R}\frac{x_3}{T_i(x,u)}\frac{p_{w,i}(T_i(x,u))-p_{w,c}}{x_1} \\ 0 \\ 0 \end{pmatrix} \quad (52)$$

$$= \begin{pmatrix} f_1(T_i(x,u), x) \\ 0 \\ 0 \end{pmatrix}$$

$$= \begin{pmatrix} \tilde{f}_1(x, u) \\ 0 \\ 0 \end{pmatrix}$$

$$y = a_{II}\begin{pmatrix} C_1(T_i, x)e^{-a_{II}(L-x_1)} + \\ C_2(T_i, x)e^{a_{II}(L-x_1)} + \\ C_4(T_i, x) + C_5(T_i, x, u) \end{pmatrix} =$$

$$= h(T_i(x, u), x, u)$$

$$= \tilde{h}(x, u)$$

Thus, a Kalman observer for the system (52) has the following structure:

$$\dot{\hat{x}} = \tilde{f}(\hat{x}, u) + S^{-1}\left(\frac{\partial \tilde{h}}{\partial x}\bigg|_{\hat{x}}\right)^T (\hat{y}-y) \quad (53)$$

$$\hat{y} = \tilde{h}(\hat{x}, u)$$

$$\dot{S} = -\left(\frac{\partial \tilde{f}}{\partial x}\bigg|_{\hat{x}}\right)^T S - S\frac{\partial \tilde{f}}{\partial x}\bigg|_{\hat{x}} + \left(\frac{\partial \tilde{h}}{\partial x}\bigg|_{\hat{x}}\right)^T \frac{\partial \tilde{h}}{\partial x}\bigg|_{\hat{x}} - S\Lambda S$$

The equation of the observer must be resolved simultaneously with the non-linear algebraic equation (51) evaluated to $x=\hat{x}$:

$$\Psi(T_i, x, u)|_{\hat{x}} = 0 \quad (54)$$

This system of equations defines an algebraic-differential problem where the algebraic part consists of equation (54).

Figure 8:
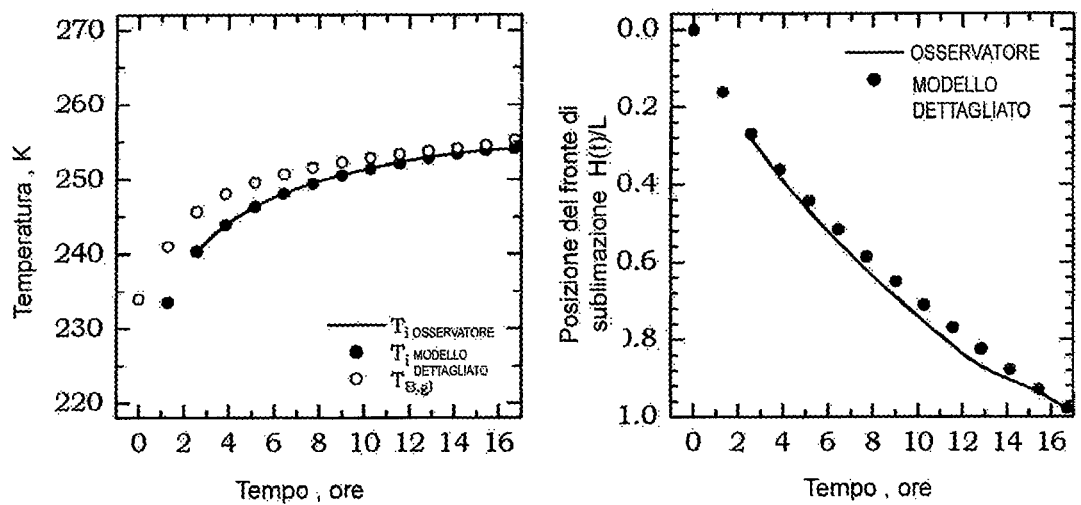
FIG. 8 shows two graphs comparing the complete model and the predictions of the Kalman state observer for reduced model II.
Figure 9:
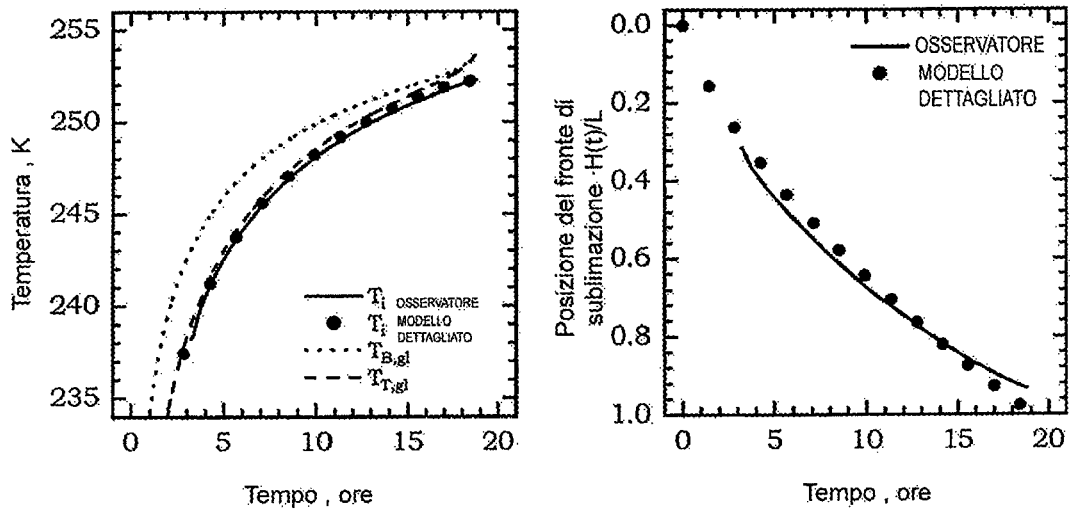
FIG. 9 shows two graphs comparing the predictions of the high gain state observer, for reduced model II, and the value provided by the detailed model of the process.

FIG. 8 reports the estimates of the temperature and the interface position provided by the Kalman observer for reduced model II, which show good agreement with the results obtained using the detailed model of the process as a real data source. The conditions and parameters used in the simulations are those reported above.

CONCLUSIONS

The first advantage of this system is that by using only one sensor 20 it is possible to obtain an entire temperature profile of the product and so deduce the position of the sublimation front, thanks to the specific calculation algorithms implemented in the system of the data processor 16.

In particular, if the measurement sensor 20 is in contact with the container exterior, the determination of product temperature is achieved non-invasively. This aspect is particularly important if the substance to be lyophilised requires operation in a sterile environment, as in this case, it would not be possible to insert thermocouples into the product due to potential contamination problems.

A further advantage of the system consists in transmitting the measurements outside the lyophilisation device without the aid of electrical cables, using technology similar to that adopted in radiofrequency devices. This way, no connections are required between the interior and exterior of the lyophilisation chamber, through the special vacuum tap with which the lyophilisation device access port 14 is provided, making installation and use of the system extremely simple.

Naturally, the principle of the invention remaining the same, the forms of implementation and details of the embodiments may be widely varied with respect to the above description illustrated purely by way of non-limiting example, without despite this departing from the scope of the invention as defined in the appended claims.

The invention claimed is:

1. System for monitoring the lyophilisation process of a product in containers arranged inside a lyophilisation chamber, comprising a temperature measurement system associated with each container housed inside the lyophilisation chamber, capable of surveying local temperature data for each container, characterised in including:
   a wireless communication system for the temperature data surveyed, comprising means of transmission inside the chamber and means of receiving outside of it; and
   means of processing of said data, located externally to the lyophilisation chamber, arranged to determine at least one parameter indicative of the progress of the lyophilisation process not measured by the measurement system, by means of a predetermined representation model of the process, capable of correlating a local temperature value of the container with said parameter.

2. System according to claim 1, wherein the temperature measuring system includes temperature sensors positioned on the inner side of the container wall.

3. System according to claim 2, wherein the temperature sensors are positioned at the base of the container wall.

4. System according to claim 1, wherein the temperature measuring system includes temperature sensors positioned on the outer side of the container wall.

5. System according to claim 1, wherein the wireless communication system comprises means of radiofrequency transmission and reception.

6. System according to claim 1, comprising means of powering the wireless temperature measuring system, by means of electromagnetic waves.

7. System according to claim 1, wherein said means of processing are programmed to select one of a plurality of lyophilisation process representation models and to determine said at least one parameter indicative of the progress of the process by means of a predetermined observer of state applied to the model.

8. System according to claim 7, wherein a first model (reduced model I) is applicable when the temperature sensors are positioned on the inner side of the container wall.

9. The system according to claim 8, wherein a state observer is of the type based on Kalman filters.

10. System according to claim 7, wherein a second model (reduced model II) is applicable when the temperature sensors are positioned on the outer side of the container wall.

11. System according to claim 10, wherein a state observer is of the high gain type.

12. System according to claim 1, wherein the parameters indicative of the progress of the lyophilisation process comprise at least one of the following: the position of the sublimation front, the temperature distribution in the volume of the product in the container, the coefficient of matter exchange in the dried product layer, the coefficient of heat exchange at the base of the container.

* * * * *